United States Patent
Ludwig

(10) Patent No.: US 7,880,886 B2
(45) Date of Patent: Feb. 1, 2011

(54) GAS SENSOR

(75) Inventor: Ronny Ludwig, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 591 days.

(21) Appl. No.: 10/583,631

(22) PCT Filed: Oct. 28, 2004

(86) PCT No.: PCT/DE2004/002399

§ 371 (c)(1),
(2), (4) Date: Sep. 9, 2008

(87) PCT Pub. No.: WO2005/062024

PCT Pub. Date: Jul. 7, 2005

(65) Prior Publication Data

US 2008/0316489 A1 Dec. 25, 2008

(30) Foreign Application Priority Data

Dec. 20, 2003 (DE) ................... 103 60 215

(51) Int. Cl.
*G01N 21/00* (2006.01)
(52) U.S. Cl. ..................... 356/437; 356/440
(58) Field of Classification Search ............. 356/437, 356/440, 442
See application file for complete search history.

(56) References Cited

U.S. PATENT DOCUMENTS 6,067,840 A * 5/2000 Chelvayohan et al. ....... 73/23.2
6,469,303 B1 * 10/2002 Sun et al. .................. 250/343
2002/0104967 A1 8/2002 Kouznetsov
2004/0188622 A1 * 9/2004 Yokura et al. ............. 250/343
2005/0161605 A1 * 7/2005 Yokura et al. ............. 250/343

FOREIGN PATENT DOCUMENTS

| DE | 195 12 126 | 9/1996 |
|----|------------|--------|
| DE | 196 45 321 | 5/1998 |
| DE | 202 03 759 | 7/2002 |
| DE | 203 01 081 | 4/2003 |
| EP | 0 825 430 | 2/1998 |
| GB | 2 262 338 | 6/1993 |
| JP | 09 184803 | 7/1997 |
| JP | 11118711 | 4/1999 |
| JP | 11 271221 | 10/1999 |
| WO | 2004 010116 | 1/2004 |
| WO | 2004 023113 | 5/2004 |

* cited by examiner

*Primary Examiner*—Roy Punnoose
(74) *Attorney, Agent, or Firm*—Kenyon & Kenyon LLP

(57) ABSTRACT

A gas sensor for measuring at least one gas concentration, in particular for a vehicle climate control system, having a substrate, an IR radiation source fastened on the substrate, an IR detector fastened on the substrate, a measurement chamber for receiving a gas having the gas concentration that is to be measured, a shielding device situated in the measurement chamber between the IR radiation source and the IR detector, for shielding a direct transmission of IR radiation from the IR radiation source to the IR detector along an optical axis, and a reflective surface that has a concavely curved first mirrored area for receiving the IR radiation emitted by the IR radiation source, and that has a concavely curved second mirrored area that reflects the IR radiation to the IR detector, the measurement chamber being formed between the reflective surface and the substrate.

22 Claims, 4 Drawing Sheets

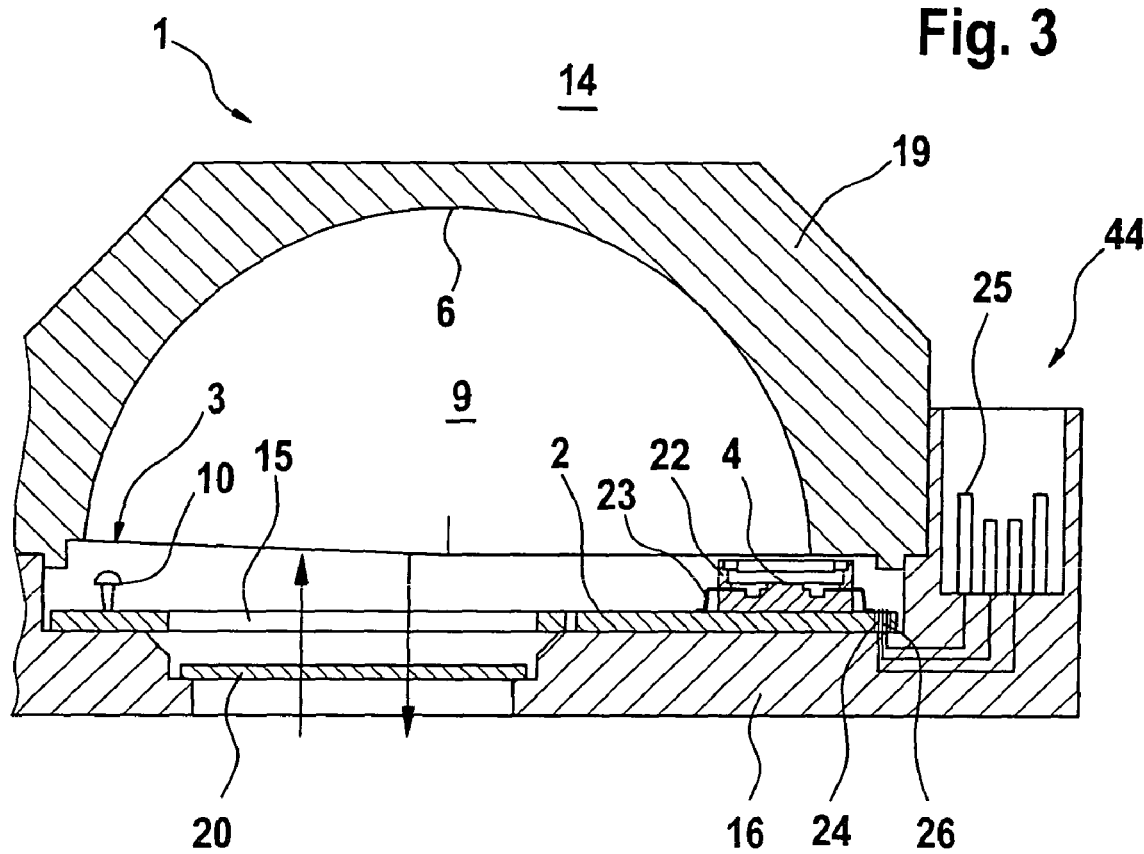
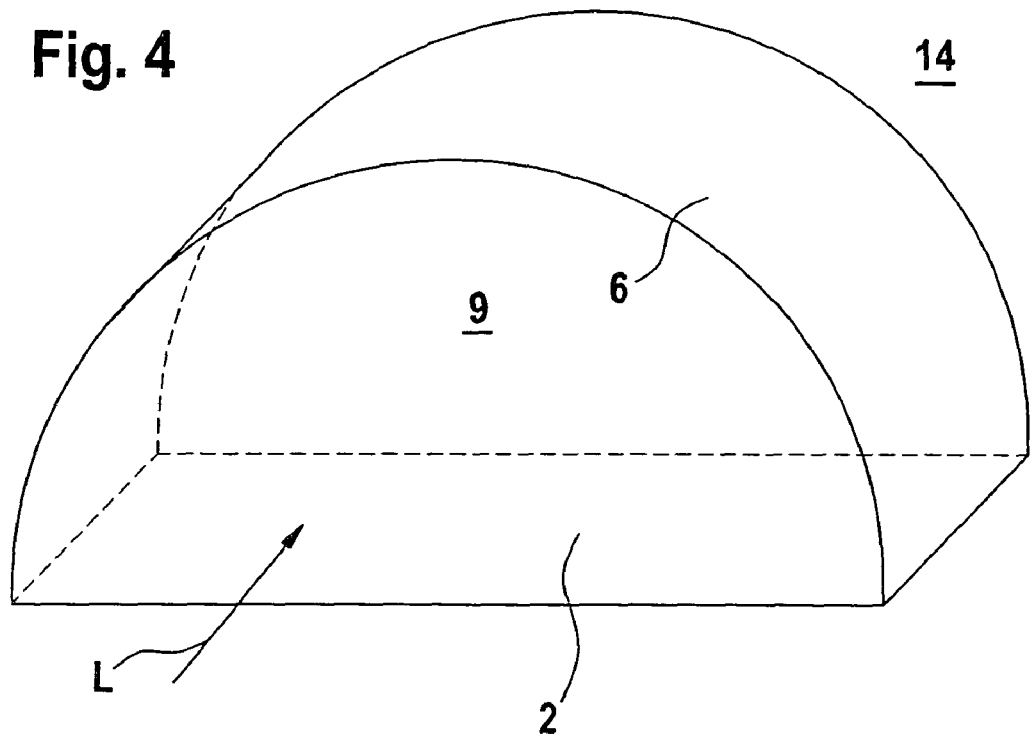

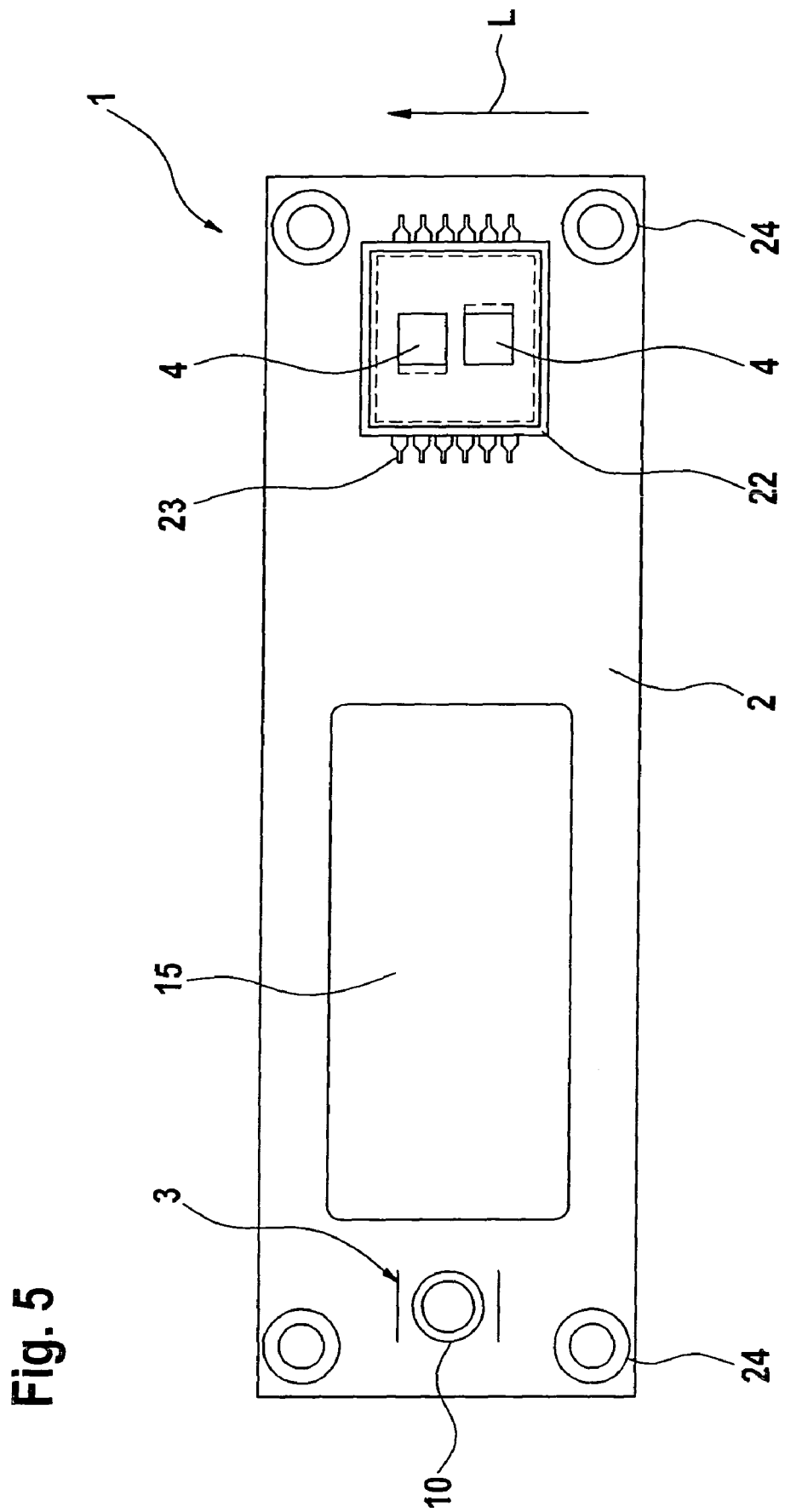

GAS SENSOR

FIELD OF THE INVENTION

The present invention relates to a gas sensor for measuring at least one gas concentration by absorption of infrared radiation in a gas.

BACKGROUND INFORMATION

Sensors for measuring a gas concentration or concentrations of various individual gases are currently used mainly for applications in medicine and biology, or in fire detection. In a spectroscopic measurement design, the fact is exploited that the various individual gases in a gas mixture each absorb IR (infrared) radiation in specific wavelength ranges. The gas concentration of an individual gas can thus be determined by measuring the absolute absorption or a relative absorption in comparison with a reference wavelength range.

In general, such gas sensors have an IR radiation source and an IR detector situated linearly opposite one another along an optical axis. The measurement area in which the relevant gas concentration is measured, i.e., in which the absorption of the IR radiation takes place, is fashioned along the optical axis between the IR radiation source and the IR detector. The IR detector generally converts the received IR radiation into a thermoelectric voltage.

For high sensitivities, in this measurement design long absorption paths, i.e. a relatively large distance between the radiation source and the detector, are advantageous. In order to achieve adequate entry of radiation into the detector element given long absorption paths, relatively strong IR radiation sources are used, which correspondingly have high power consumption. For applications in automotive technology in particular, however, high power consumption is not desirable. In addition, given high power levels and a compact construction of the gas sensor in which the IR radiation source and the IR detector are installed as a common module, a gradual heating takes place that falsifies the measurement signal measured via the thermoelectric voltage. This can be compensated only at high expense.

For shorter absorption paths, the measurement signal, in particular the signal-noise ratio, is low. By using reflective surfaces, the absorption path can at first be enlarged, but in general the reflectors required for this result in additional costs; in addition, an optical adjustment, and possibly also a subsequent correction of the situation of the reflectors, is required. Because part of the IR radiation is absorbed when there is reflection at the reflective surfaces, and there are also reflection losses due to scatter, the measurement signal is in turn decreased. In addition, dead areas not covered by the gas circulation can form on the reflectors, making a dynamic measurement process more difficult.

SUMMARY OF THE INVENTION

In contrast, the gas sensor according to the present invention has in particular the advantage that a simple, economical, and compact design is possible, while nonetheless making possible a large measurement signal, in particular having a high signal-noise ratio, with good dynamic measurement characteristics.

Because the IR radiation source and the IR detector are attached to a common substrate, preferably a circuit board, a rapid and economical manufacture is possible, e.g. using standard placement methods of circuit board technology. In particular, assembly on a single side of a substrate is advantageous here. The shielding device prevents a direct signal transmission between the IR radiation source and the IR detector, so that the measurement takes place via the mirrored areas, which according to the present invention have a concave curvature.

The curved, concave mirrored areas enlarge the effective measurement area without an expansion of the beam path; advantageously, it is even possible to effect a bundling and thus an increase in intensity. The measurement space is formed between the reflective surface and the substrate, and can in this way be fashioned so as to be voluminous while nonetheless having a compact construction.

The assembly of additional optical components on the substrate is not required. The reflective surface can be assembled without expensive adjustment and subsequent correction, because its position relative to the substrate, and thus also relative to the detector and the radiation source, can easily be fixed. Here, in the assembly on a circuit board an electrical assembly that is immediately capable of functioning is formed that can be tested directly before being installed in the surrounding housing.

The reflective surface can be formed as the inside of a reflector that is fastened directly on the substrate, or on the IR radiation source and the IR detector and thus indirectly on the substrate. Alternatively, the reflective surface can also be formed as the inner surface of a housing cover. Because additional optical components are not required, a simple, compact design results.

The overall circuit can be connected to the exterior via cold contacting technology, e.g. by press-fit pins between the circuit board and the housing, so that an economical, reliable and fast contacting is possible in one operational step.

With the use of a reflective surface having a spherical cross-section, in particular a cylindrical reflective surface, an absorption path can be realized that is long in relation to the overall size of the housing. Due to the fact that the radiation source is situated very close to the reflective surface, the low angle of incidence on the reflective surface results in very low radiation losses, e.g. approximately 4%. Due to this, a radiation source can be chosen having low power consumption or lower radiated power, thus reducing the power consumption. With such a semicircular or cylindrical inner surface, an optimal gas distribution in the measurement chamber can be achieved in which no dead volumes or gas sumps are formed. This makes a precise, dynamic measurement possible.

With the use of parabolic mirrored areas, in the measurement chamber a large effective measurement area can be formed with high signal intensity due to the strong bundling of the IR radiation.

According to the present invention, a plurality of detector areas can be situated one after the other in the longitudinal direction.

BRIEF DESCRIPTION OF THE DRAWINGS

FIG. 3 shows a section through a gas sensor according to another specific embodiment, having a cylindrical reflective surface fastened to or integrated into the housing cover.

FIG. 4 shows a perspective view of the reflective surface of the sensor from FIG. 3.

FIG. 5 shows a top view of a specific embodiment of a circuit board, having a gas feedthrough opening, of the gas sensors according to the present invention.

DETAILED DESCRIPTION

Figure 1:
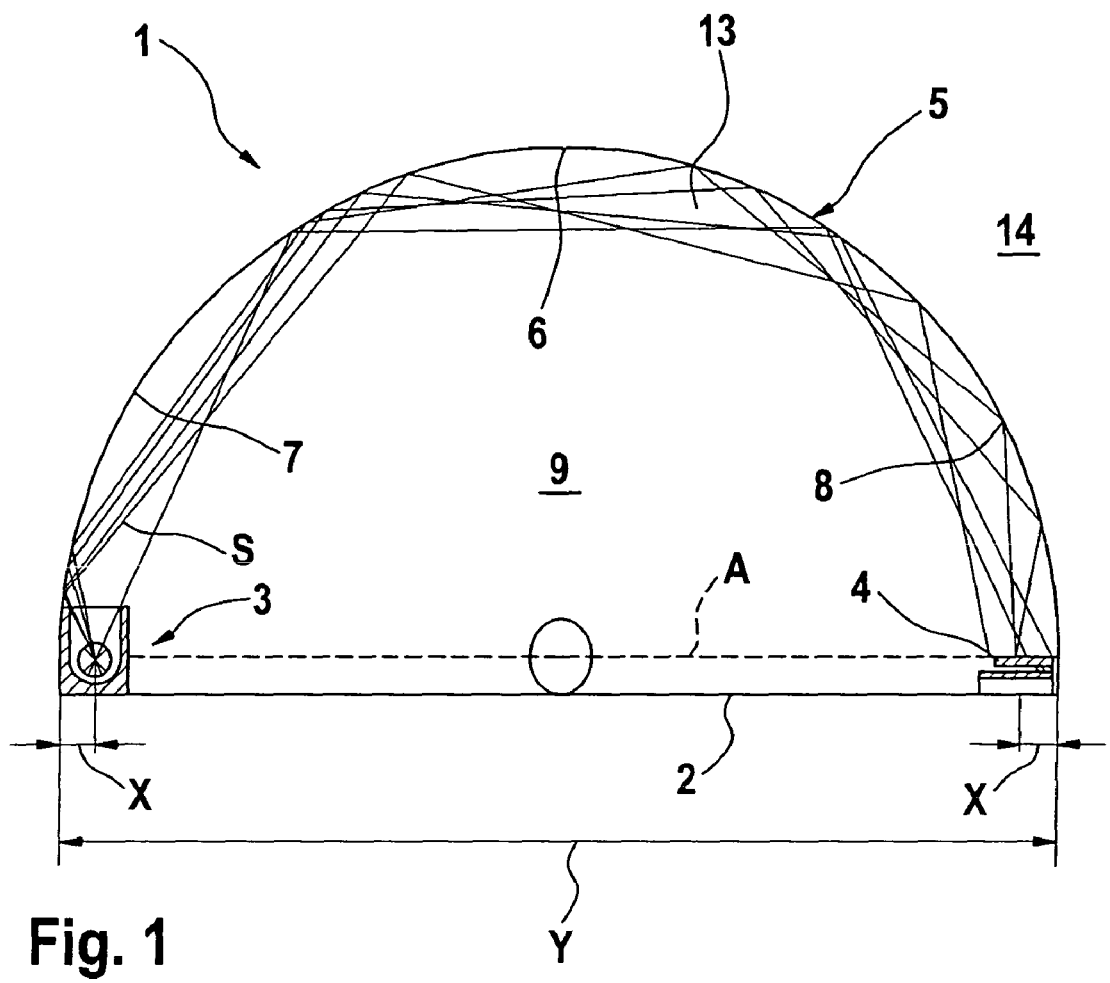
FIG. 1 shows a section through the gas sensor according to the present invention having a cylindrical reflective surface.

A gas detector 1 has a circuit board 2 that acts as a substrate, an IR radiation source 3 attached to circuit board 2, and an IR detector 4 attached to circuit board 2. In addition, a reflector 5 is provided having a half-cylindrical reflective surface 6 that together with circuit board 2 encloses a measurement chamber 9 in which one or more gas concentrations are measured. Reflective surface 6 according to the present invention reflects radiation at least in the relevant infrared range, and can preferably be fashioned as a metallic layer or a metallic coating, or can be fashioned completely from metal.

Figure 2:
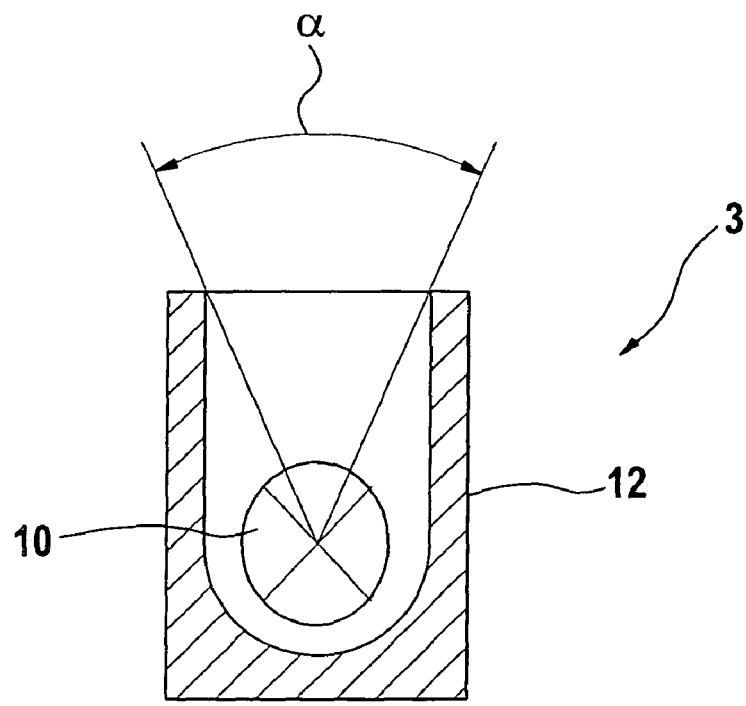
FIG. 2 shows an enlargement of a detail of the IR radiation source from FIG. 1.

IR radiation source 3, shown in detail in FIG. 2, has an IR lamp 10, e.g., a bulb or an IR LED, and has a small housing 12 that acts as a shielding device according to the present invention that only permits IR radiation to exit at a radiation angle α that is preferably 40° to 60°, e.g. 50°. IR radiation source 3 and IR detector 4 are situated close to cylindrical reflective surface 6; i.e., the distance X of reflective surface 6 from IR radiation source 3 and from IR detector 4 is very small in relation to the circular diameter Y of reflective surface 6; preferably this ratio is 1:20 to 1:40, e.g. 1:32, so that further transmission of radiation takes place only close to the surface. Small housing 12 on the one hand prevents a direct transmission of IR radiation from IR radiation source 3 to IR detector 4 along optical axis A, and on the other hand permits IR radiation to exit only at a flat angle of reflection to cylindrical reflective surface 6. Here, the angle of reflection at reflective surface 6 is for example in a range from 20° to 40°, e.g. approximately 30°. The IR radiation is reflected from cylindrical reflective surface 6 multiple times, e.g. approximately two to four times according to FIG. 1, before it reaches IR detector 4. IR detector 4 can for example be fashioned as a thermopile element that measures the received IR radiation as a thermal difference and emits it as a thermoelectric voltage. Alternatively, other IR detectors can also be provided. In the depicted gas detector according to the present invention, an influence of foreign radiation is largely excluded due to the shielding of measurement chamber 9 by circuit board 2 and reflective surface 6. In the measurement of at least one gas concentration, only one radiation filter is required, optionally in the area of the radiation source or before the detector, or integrated into the detector. If measurement of various gas concentrations is to take place in a gas-specific fashion, detector 4 can correspondingly be divided into a plurality of detector areas provided with specific radiation filters that measure the absorption in the respective wavelength ranges.

In this specific embodiment, the IR radiation fills only a narrow measurement area 13 that extends along reflective surface 6; the inner area of measurement chamber 9 is not used for the detection of the gas. Due to the small angle of reflection, only a small absorption of the IR radiation takes place at reflective surface 6, so that a high signal is achieved despite multiple reflections. In addition, in the depicted design practically all the radiation emitted by radiation source 3 is acquired by IR detector 4.

In the specific embodiments, the gas exchange between measurement chamber 9 and an external chamber 14 can take place on the one hand in the longitudinal direction, i.e. parallel to the surface of circuit board 2 and perpendicular to optical axis A. In addition, a gas exchange is possible via gas feedthrough openings 15 that run through circuit board 2. In principle, gas feedthrough openings through reflector 5 are also possible by forming this reflector as a lattice in some areas.

In the specific embodiment of FIG. 3, circuit board 2 is attached to a housing lower part 16 on which a housing cover 19 is placed in radiation-tight fashion. Here, reflective surface 6 is fashioned on the concave inner side of housing cover 19, e.g. by fusing it into housing cover 19 or by vapor deposition of a metallic layer onto the cylindrical inner surface of housing cover 19.

In this specific embodiment, the gas exchange between measurement chamber 9 and external chamber 14 is possible on the one hand in longitudinal direction L, as can be seen in FIG. 4; however, a construction is also possible having a sealed front and back side, and thus without a gas exchange in longitudinal direction L. In addition, a gas exchange is possible through a gas feedthrough 15 in circuit board 10, which is sealed by a porous membrane 20.

In the embodiment shown in FIG. 3, the shielding device is provided not at IR radiation source 3, but rather at IR detector 4. For this purpose, IR detector 4, fashioned as a thermopile chip, is placed into a small housing 22 that is contacted with circuit board 2 via connecting pins 23. IR radiation source 3 can here be fashioned as a simple, non-shielded lamp 10. In this specific embodiment having cylindrical reflective surface 6, IR radiation source 3 and IR detector 4 are also situated close to reflective surface 6, e.g. also underneath reflective surface 6 in some areas.

The fastening and contacting of circuit board 2 on housing lower part 16 can preferably take place via a cold contacting technology, as can be seen from the section of FIG. 3 and the top view of circuit board 2 of FIG. 5. Here, at least one press-fit bushing 24 is formed on circuit board 2 that is connected to connecting pins 23 via printed conductors (not shown) and diepads. A firm seating of circuit board 2 can be achieved through the formation of four press-in bushings 24, due to their position and arrangement. Press-in bushing 24 is plugged into press-in pins 26 of housing lower part 16, which are connected to contacts 25 of a connecting bushing 44 of housing lower part 16, as is indicated in the schematic representation of FIG. 3. The supply of power and the signal reception from detector chip 4, as well as the supply of power to IR radiation source 3, take place via contacts 25.

As can be seen from FIG. 5, a plurality of detectors 4 are preferably situated one after the other in the longitudinal direction L, e.g. for measuring one or more relevant wavelength ranges and a reference wavelength range in order to enable a relative measurement. The situating of a plurality of detectors is facilitated by the elongated, e.g. cylindrical, construction in longitudinal direction L, the beam paths of the IR radiation S being situated close to one another so that the flow conditions of the gas correspond to one another and errors due to different gas or flow conditions are at least very low.

Figure 6:
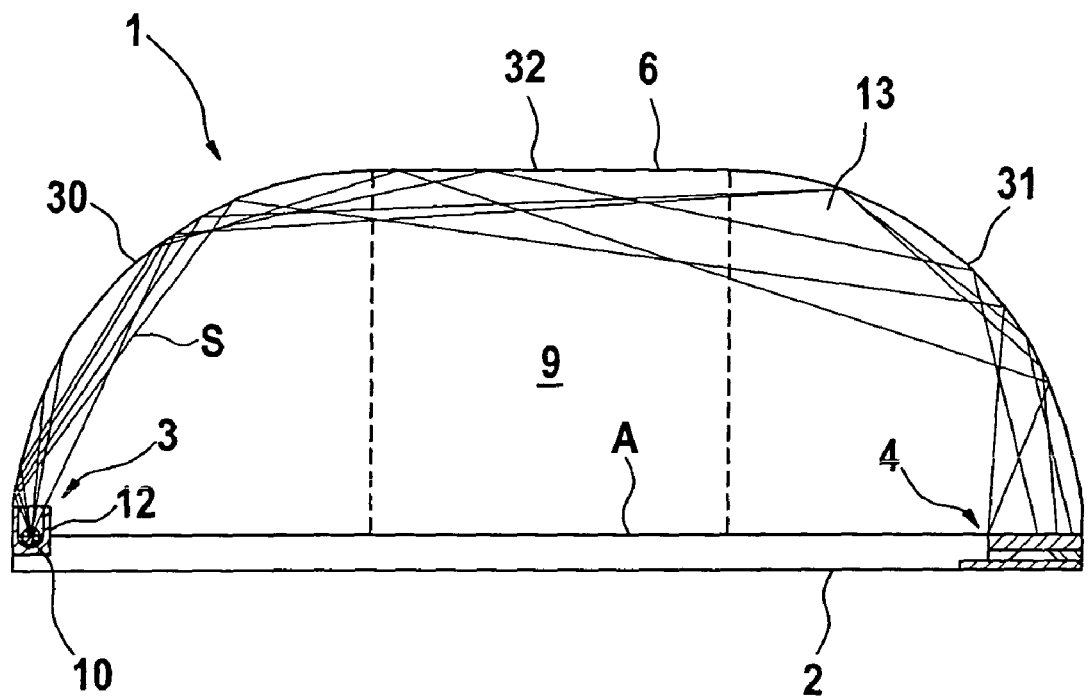
FIG. 6 shows a section through a gas sensor according to a further specific embodiment, having a reflective surface that has two spherical mirrored areas.

In the embodiment shown in FIG. 6, IR radiation source 3 and IR detector 4 are each situated at a spherical mirrored area 30, 31 of reflective surface 6, mirrored areas 30, 31 being connected via a flat middle surface area 32. In this specific embodiment as well, reflective surface 6, shown in section, extends in longitudinal direction L, so that surface areas 30, 31 are fashioned cylindrically.

IR radiation source 3 and detector 4 are in turn situated close to spherical mirrored areas 30, 31, e.g. with the same ratio of distance X to circular diameter Y of the spherical mirrored areas as described in FIG. 1. The shielding device formed by small housing 12 of IR radiation source 3 lets through only that part of radiation S of IR lamp 10 that is directed onto spherical mirrored area 30. In this specific embodiment, in contrast to the specific embodiment of FIGS. 1 to 4, in principle a larger number of reflections are permitted at reflective surface 6 formed from mirrored areas 30, 31, 32; here as well, the reflection takes place at relatively small angles of reflection, so that the absorption, and thus the loss of signal intensity, is low. Measurement area 13 is correspondingly enlarged by flat middle mirrored area 32. In this specific embodiment as well, reflective surface 6 can be fashioned by a reflector 5, fastened on circuit board 2 or on IR radiation source 3 and on detector 4, or can be fashioned as the inner surface of a housing cover.

Figure 7:
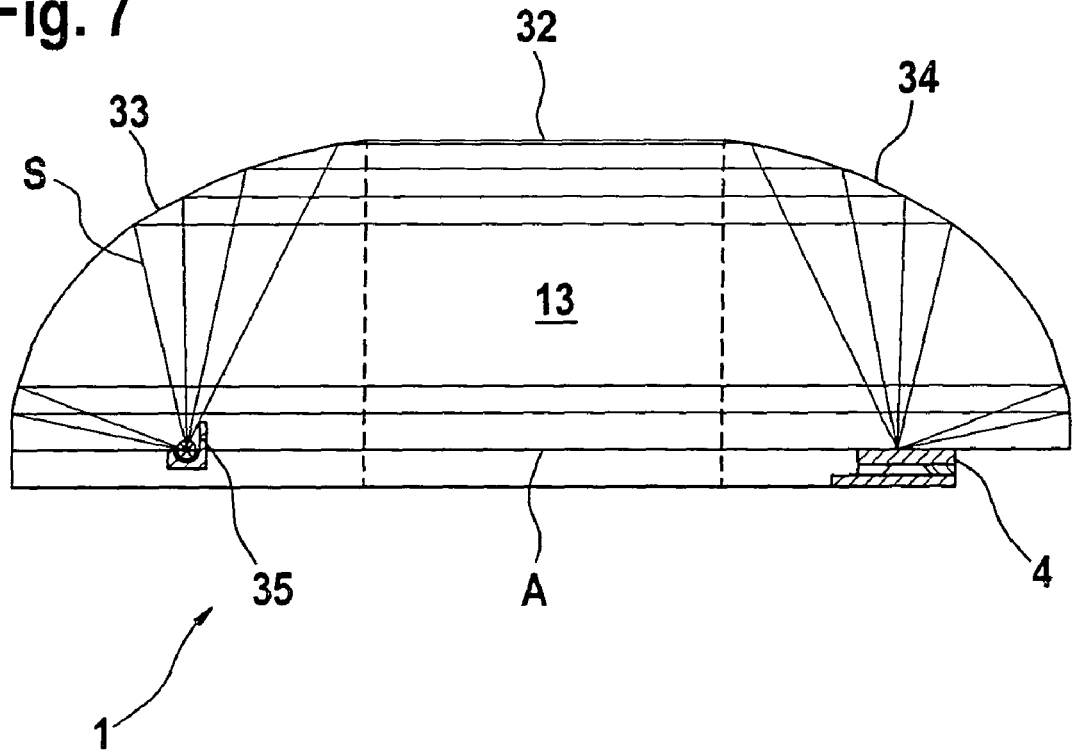
FIG. 7 shows a section through a gas sensor according to a further specific embodiment, having two parabolic mirrored areas.

In the embodiment shown in FIG. 7, IR radiation source 3 and detector 4 are situated in the focus of parabolic mirrored areas 33, 34, which are connected via a flat middle surface area 32 and are situated on a common optical axis A. Middle flat area 32 can in turn be fashioned as a mirrored area; in principle, however, in this specific embodiment a non-mirroring surface area 32 is also possible.

Small housing 35, which acts as a shielding device, lets radiation S through only to parabolic mirrored area 33, surrounding radiation source 3, of reflective surface 6, so that radiation S is reflected by parabolic mirrored area 33 parallel to optical axis A, ideally no radiation impinges on middle surface area 32, and incident radiation S is bundled onto detector 4 completely by second parabolic mirrored area 34 surrounding detector 4. In this specific embodiment, measurement area 13, through which radiation S passes, ideally fills measurement chamber 9 formed between circuit board 2 and reflective surface 6 almost completely.

In the embodiment of FIG. 7, exactly two reflections of IR radiation S therefore take place, namely at parabolic mirrored areas 33 and 34. Focusing onto a smaller area of detector 4 is possible. However, in this specific embodiment the reflection takes place at a larger angle of reflection, and thus possibly with larger radiation losses than in the specific embodiments of FIGS. 1 to 6.

What is claimed is:

1. A gas sensor for measuring at least one gas concentration for a vehicle climate control system, comprising:
   a substrate;
   an IR radiation source fastened on the substrate;
   an IR detector fastened on the substrate;
   a measurement chamber for receiving a gas having the gas concentration that is to be measured;
   a shielding device situated in the measurement chamber between the IR radiation source and the IR detector, for shielding a direct transmission of IR radiation from the IR radiation source to the IR detector along an optical axis; and
   a reflective surface that has a concavely curved first mirrored area for receiving the IR radiation emitted by the IR radiation source, and that has a concavely curved second mirrored area that reflects the IR radiation to the IR detector, wherein the measurement chamber is formed between the reflective surface and the substrate;
   wherein the IR radiation source emits IR radiation at an angle of incidence of less than 45° to the first mirrored area.

2. The gas sensor as recited in claim 1, wherein the first mirrored area and the second mirrored area are fashioned with a spherical cross-section.

3. The gas sensor as recited in claim 2, wherein the reflective surface is fashioned so as to be essentially semicircular.

4. The gas sensor as recited in claim 2, wherein the reflective surface has a first spherical mirrored area, a second spherical mirrored area situated at a distance from the first spherical mirrored area in the direction of the optical axis, and a flat middle mirrored area that connects the spherical mirrored areas.

5. The gas sensor as recited in claim 1, wherein the IR radiation source and the IR detector are adjacent to the reflective surface.

6. The gas sensor as recited in claim 1, wherein the reflective surface has a first parabolic mirrored area in whose focus the IR radiation source is situated, and has a second parabolic mirrored area in whose focus the IR detector is situated.

7. The gas sensor as recited in claim 6, wherein the parabolic mirrored areas are situated at a distance from one another in the direction of the optical axis, and are connected via a straight surface area.

8. The gas sensor as recited in claim 7, wherein the straight surface area is fashioned as a reflecting mirrored area.

9. The gas sensor as recited in claim 1, wherein the shielding device is fashioned at or as part of the IR radiation source as a small housing that surrounds an IR lamp.

10. The gas sensor as recited in claim 1, wherein the shielding device is fashioned at or as part of the IR detector as a small housing that surrounds the IR detector.

11. The gas sensor as recited in claim 1, wherein the substrate is a circuit board.

12. The gas sensor as recited in claim 1, wherein the reflective surface extends uniformly in a longitudinal direction that is parallel to the substrate surface and that runs orthogonal to the optical axis.

13. The gas sensor as recited in claim 1, wherein the first mirrored area and the second mirrored area are fashioned with a spherical cross-section, wherein the reflective surface has a first spherical mirrored area, a second spherical mirrored area situated at a distance from the first spherical mirrored area in the direction of the optical axis, and a flat middle mirrored area that connects the spherical mirrored areas, and wherein the IR radiation source and the IR detector are adjacent to the reflective surface.

14. The gas sensor as recited in claim 13, wherein the shielding device is fashioned at or as part of the IR radiation source as a small housing that surrounds an IR lamp.

15. The gas sensor as recited in claim 13, wherein the shielding device is fashioned at or as part of the IR detector as a small housing that surrounds the IR detector.

16. The gas sensor as recited in claim 13, wherein the reflective surface extends uniformly in a longitudinal direction that is parallel to the substrate surface and that runs orthogonal to the optical axis.

17. The gas sensor as recited in claim 13, wherein a single IR radiation source and at least two detectors situated one after the other in the longitudinal direction are provided.

18. The gas sensor as recited in claim 1, wherein the reflective surface has a first parabolic mirrored area in whose focus the IR radiation source is situated, and has a second parabolic mirrored area in whose focus the IR detector is situated, wherein the parabolic mirrored areas are situated at a distance from one another in the direction of the optical axis, and are connected via a straight surface area, and wherein the straight surface area is fashioned as a reflecting mirrored area.

19. The gas sensor as recited in claim 18, wherein the shielding device is fashioned at or as part of the IR radiation source as a small housing that surrounds an IR lamp.

20. The gas sensor as recited in claim 18, wherein the shielding device is fashioned at or as part of the IR detector as a small housing that surrounds the IR detector.

21. The gas sensor as recited in claim 18, wherein the reflective surface extends uniformly in a longitudinal direction that is parallel to the substrate surface and that runs orthogonal to the optical axis.

22. The gas sensor as recited in claim 18, wherein a single IR radiation source and at least two detectors situated one after the other in the longitudinal direction are provided.

* * * * *